(12) United States Patent
Shalaby

(10) Patent No.: US 7,192,437 B2
(45) Date of Patent: *Mar. 20, 2007

(54) HIGH STRENGTH FIBERS OF L-LACTIDE COPOLYMERS, ε-CAPROLACTONE, AND TRIMETHYLENE CARBONATE AND ABSORBABLE MEDICAL CONSTRUCTS THEREOF

(75) Inventor: Shalaby W. Shalaby, Anderson, SC (US)

(73) Assignee: Poly Med Inc, Anderson, SC (US)

( * ) Notice: Subject to any disclaimer, the term of this patent is extended or adjusted under 35 U.S.C. 154(b) by 1349 days.

This patent is subject to a terminal disclaimer.

(21) Appl. No.: 09/862,093

(22) Filed: May 21, 2001

(65) Prior Publication Data

US 2001/0051814 A1 Dec. 13, 2001

Related U.S. Application Data

(63) Continuation-in-part of application No. 09/523,754, filed on Mar. 13, 2000, now Pat. No. 6,342,065.

(60) Provisional application No. 60/124,838, filed on Mar. 17, 1999.

(51) Int. Cl.
 *A61L 17/00* (2006.01)
 *A61B 17/04* (2006.01)
 *C08G 63/08* (2006.01)

(52) U.S. Cl. ............ 606/230; 606/231; 525/415; 528/354

(58) Field of Classification Search ........ 606/228, 606/230, 231, 2; 528/354, 357; 424/426; 525/415

See application file for complete search history.

(56) References Cited

U.S. PATENT DOCUMENTS

| 4,429,980 | A | 2/1984 | Miller | 354/311 |
| 4,605,730 | A | 8/1986 | Shalaby et al. | 528/357 |
| 4,700,704 | A | 10/1987 | Jamiolkowski et al. | 128/335.5 |
| 5,425,984 | A | 6/1995 | Kennedy et al. | 428/229 |
| 6,342,065 | B1 * | 1/2002 | Shalaby | 606/230 |

FOREIGN PATENT DOCUMENTS

| DE | 43 00 420 A1 | 7/1994 |
| EP | 0 241 252 A2 | 10/1987 |
| EP | 0 500 098 A2 | 8/1992 |
| WO | WO 94/11441 | 5/1994 |

OTHER PUBLICATIONS

S.W. Shalaby and R.A. Johnson, Chap. 1 (*Synthetic Absorbable Polyesters*), pp. 1-34, *Biomedical Polymers*, (Shalaby, Ed.), Hanser Publishing, NY, 1994.

B.C. Benicewicz, et al., Chap. 14, vol. 433 (*In Vitro and In Vivo Degradation of Poly(L-lactide) Braided Multifilament Yarns*); pp. 161-166, *ACS Symp. Series*, Am. Chemical Soc., Washington, DC, 1990.

* cited by examiner

*Primary Examiner*—Kim M. Lewis
(74) *Attorney, Agent, or Firm*—Leigh P Gregory

(57) ABSTRACT

The present invention is directed to crystalline copolymers of l-lactide and a minor portion of a cyclic monomer, preferably ε-caprolactone or trimethylene carbonate or both. The present copolymers have a melting temperature of at least 150° C. and a crystallinity of at least 20%. Preferred are high molecular weight copolymers having an inherent viscosity of at least 1.1 dl/g. A variety of surgical constructs may be formed from the present copolymers. Surgical sutures made of mono- or multifilament yarns of the present copolymers will bioabsorb in less than three years and will maintain at least 50% of their initial strength three weeks post-operatively.

14 Claims, No Drawings

US 7,192,437 B2

HIGH STRENGTH FIBERS OF L-LACTIDE COPOLYMERS, ε-CAPROLACTONE, AND TRIMETHYLENE CARBONATE AND ABSORBABLE MEDICAL CONSTRUCTS THEREOF

BACKGROUND OF THE INVENTION

The present application is a continuation-in-part of U.S. Ser. No. 09/523,754, filed Mar. 13, 2000, now U.S. Pat. No. 6,342,065 which claims benefit of provisional U.S. Ser. No. 60/124,838, filed Mar. 17, 1999.

It is well established in the prior art that absorbable fibers suitable for constructing biomedical constructs with prolonged strength retention profile, as in certain surgical sutures and meshes as well as prosthetic tendons and ligaments, need to be based on polymers having (1) high molecular weight; (2) a high degree of crystallinity; and (3) minimum or no monomeric species. These requirements were claimed to have been fulfilled by the l-lactide/glycolide copolymers described in U.S. Pat. No. 5,425,984 and EP Application No. 241,252 (1987). However, in certain high load-bearing applications where a prosthetic fibrous construct experiences cyclic stresses and is expected to maintain a substantial fraction of its initial strength for several weeks post-operatively, additional requirements are imposed. Typical examples of such constructs are surgical meshes for hernia repair and prosthetic tendons and ligaments. These additional requirements are expected to be associated with having a high degree of toughness, as measured in terms of the work required to break, without compromising, significantly, their high tensile strength, high elastic modulus, low stretchability, and high yield strength. Such requirements also are expected to be associated with a polymeric chain with higher hydrolytic stability than those containing glycolate sequences are. Unfortunately, the prior art of absorbable polymers provides conflicting teachings that may be applied towards meeting the aforementioned additional requirements. To increase toughness, the introduction of more flexible ε-caprolactone-based sequences in polyglycolide chain has been used successfully in the production of low modulus sutures (see, for example, U.S. Pat. Nos. 4,605,730 and 4,700,704) but with compromised strength. A similar situation is encountered in the copolymer of glycolide and trimethylene carbonate (see, for example, U.S. Pat. No. 4,429,980). Interestingly, fibers made of these two types of copolymers do display a lower propensity to hydrolysis than polyglycolide, but their strength loss profiles remain unsuitable for long-term, load-bearing applications. Unexpectedly, the present invention describes copolymeric caprolactone and trimethylene carbonate based compositions, which meet the above noted stringent requirement for fibers suited for the construction of biomedical devices, and particularly surgical ligatures or sutures, that are expected to (1) support high loads; (2) experience cyclic stresses; (3) display minimum or average stretchability; (4) display a high degree of toughness; (5) display optimum hydrolytic stability; and (6) possess a prolonged strength profile, particularly during the initial post-operative period, as braided multifilament or monofilament sutures.

SUMMARY OF THE INVENTION

The present invention is directed to a crystalline copolymer which is a copolymer of l-lactide and at least one cyclic monomer which is a liquid at or above about 40° C., wherein the l-lactide derived sequences of the polymer chain comprise from about 60 to about 99 percent of all sequences, and wherein the copolymer has a $T_m$ of at least 150° C., exhibits a crystallinity of at least about 20%, and has an inherent viscosity of at least about 1.1 dl/g.

Preferably the cyclic monomer is ε-caprolactone, trimethylene carbonate, or both. Molar ratios of l-lactide to cyclic monomer which are within the scope of the present invention include 60 to 40, 62 to 38, 65 to 35, 68 to 32, 72 to 28, 76 to 24, 80 to 20, 84 to 16, 85 to 15, 86 to 14, 90 to 10, 95 to 5, and 99 to 1.

Preferably, the copolymers, subject of this invention, wherein the l-lactide-based repeat units constitute about 95% of the chain, such units are randomly linked to one or two types of repeat units based on trimethylene carbonate and/or ε-caprolactone. More preferably, the copolymers, subject of this invention, wherein the l-lactide-based repeat units constitute about 65 to 94% of the chain, such units are present as crystallizable segments or blocks.

A monofilament suture made from the copolymer of the present invention has an elastic modulus of greater than about 400,000 psi, a tensile strength of greater than about 40,000 psi, and a percent elongation of less than about 50%.

A monofilament suture made from the copolymer of the present invention has an elastic modulus of greater than about 100,000 psi, a tensile strength of greater than about 40,000 psi, and percent elongation of less than 80%.

Also within the scope of the present invention are multifilament yarns made from the copolymer of the present invention. Such multifilament yarns which may be employed as surgical sutures or may be formed into a surgical device or construct such as, for example, a mesh, a prosthetic tendon, a ligament or a vascular graft.

DETAILED DESCRIPTION OF PREFERRED EMBODIMENTS

The present invention is directed to high molecular weight copolymers of a major portion of l-lactide and a minor portion of ε-caprolactone (CL) or trimethylene carbonate (TMC) or both. High molecular weight is defined as displaying an inherent viscosity of at least 1.1 dl/g. The molar ratio of l-lactide to comonomer is between from about 60 to about 40% and from about 99 to about 1%. Preferably, the ratio is between from about 65 to about 35% and from about 95 to about 5%. More preferably, the ratio is between from about 75 to about 25% and from about 90 to about 10%. Most preferably the ratio is between from about 80 to about 20% and from about 85 to about 15%. The present copolymers, particularly the l-lactide/caprolactone copolymers of the present invention, have a degree of crystallinity of greater than about 20%.

The present invention is also directed to l-lactide/caprolactone, l-lactide/trimethylene carbonate and l-lactide/caprolactone/trimethylene carbonate-based monofilament yarn having a Young's modulus of more than 400,000 psi, a tensile strength exceeding 40,000 psi, a percent elongation of less than 50%, a $T_m$ of greater than about 150° C., and a degree of crystallinity exceeding 25%.

The present invention is also directed to l-lactide/ε-caprolactone, l-lactide/trimethylene carbonate, and l-lactide/ε-caprolactone/trimethylene carbonate-based monofilament yarn having a Young's modulus of more than 100,000 psi, a percent elongation of less than 80%, a $T_m$ of greater than 150° C., and degree of crystallinity exceeding 20%.

The present invention is also directed to l-lactide/ε-caprolactone, l-lactide/trimethylene carbonate, and l-lactide/ε-caprolactone/trimethylene carbonate-based monofilament yarn having l-lactide-based units constituting about 60 to 99% of the total chain repeat units and present in crystallizable segments or blocks.

The present invention is also directed to l-lactide/ε-caprolactone, l-lactide/trimethylene carbonate, and l-lactide/ε-caprolactone/trimethylene carbonate-based monofilament yarn having l-lactide-based units constituting about 95% of the total chain repeat units and linked at random with ε-caprolactone and/or trimethylene carbonate-based units.

The present invention is also directed to multifilament yarn having a tenacity in excess of 3 g/d with single fiber diameter of less than 35μ. In accordance with the present invention, surgical suture made of such monofilament and multifilament yarns absorb in less than 3 years and maintain at least 50% of their initial strength at three weeks post-operatively, preferably at six weeks post-operatively. Also within the scope of the present invention are prosthetic ligaments, tendons, meshes for tissue repair, and vascular grafts made totally of such multifilament yarns or a combination the present multifilaments and monofilaments or a combination with other more absorbable multifilament or monofilament yarns.

The present invention is also directed to multifilament yarn having a tenacity in excess of 2 g/d with single fiber diameter of less than 40μ. In accordance with the present invention, surgical suture made of such monofilament and multifilament yarns absorb in less than 3 years and maintain at least 50% of their initial strength at four weeks post-operatively, preferably at four weeks post-operatively. Also within the scope of the present invention are prosthetic ligaments, tendons, meshes for tissue repair, and vascular grafts made totally of such multifilament yarns or a combination the present multifilaments and monofilaments or a combination with other more absorbable multifilament or monofilament yarns.

The following Examples are representative of preferred copolymers of the present invention and exemplary applications thereof.

EXAMPLE 1

Preparation of 50/50 ε-Caprolactone/Trimethylene Carbonate Initiated by 1,3-Propanediol The reaction apparatus was comprised of a 3-neck 500 ml boiling flask equipped with a penny-head stopper, a magnetic stir bar, and two 90° connectors. After obtaining a vacuum of 0.05 mmHg, the apparatus was flame dried under argon purge. An initial charge of 122.9 grams (1.204 moles) of trimethylene carbonate was added to the flask.

The apparatus and its contents were placed under room temperature vacuum for 1 hour and 15 minutes. The system was then purged with argon. Using a high temperature oil bath, the apparatus and its contents were heated to 100° C. Upon complete melting of the trimethylene carbonate, the additional charge of 137.5 grams (1.204 moles) ε-caprolactone, 1.3 grams ($1.605 \times 10^{-2}$ moles) of 1,3-propanediol, and 1.72 milliliters ($3.44 \times 10^{-4}$ moles) of a 0.2 M solution of stannous octoate catalyst in toluene was added to the kettle while stirring. The temperature was then increased to 180° C. Reaction was maintained at 180° C. for 1.5 hours.

The molecular weights were determined by GPC using Dichloromethane as solvent. The results were as follows: Mn=31.6 kiloDaltons, Mw=58.9 kiloDaltons, and Mp=70.0 kiloDaltons.

EXAMPLE 2

Preparation of 80/20 ε-Caprolactone/Trimethylene Carbonate Initiated by 1,3-Propanediol The reaction apparatus was comprised of a 3-neck 500 ml boiling flask equipped with a penny-head stopper, a magnetic stir bar, and two 90° connectors. After obtaining a vacuum of 0.15 mmHg, the apparatus was flame dried under argon purge. An initial charge of 55.2 grams (0.538 moles) of trimethylene carbonate was added to the flask.

The apparatus and its contents were placed under room temperature vacuum for 1 hour. The system was then purged with argon. Using a high temperature oil bath, the apparatus and its contents were heated to 100° C. Upon complete melting of the trimethylene carbonate, the additional charge of 245.3 grams (2.15 moles) ε-caprolactone, 1.3 milliliters ($1.792 \times 10^{-2}$ moles) of 1,3-propanediol, and 1.92 milliliters ($3.84 \times 10^{-4}$ moles) of a 0.2 M solution of stannous octoate catalyst in toluene was added to the flask while stirring. The temperature was then increased to 180° C. Reaction was maintained at 180° C. for 1 hour.

The molecular weights were determined by GPC using Dichloromethane as solvent. The results were as follows: Mn=45.8 kiloDaltons and Mw=76.1 kiloDaltons.

EXAMPLE 3

Preparation of Poly-ε-Caprolactone Initiated by 1,3-Propanediol

The reaction apparatus was comprised of a 1-neck 500 ml boiling flask equipped with a 90° connector and a magnetic stir bar. The apparatus was flame dried under nitrogen. An initial charge of 400.1 grams (3.509 moles) of ε-caprolactone, 1.69 milliliters ($2.339 \times 10^{-2}$ moles) 1,3-propanediol, and 2.51 milliliters ($5.01 \times 10^{-2}$ moles) of a 0.2 M solution of stannous octoate catalyst in toluene was added to the flask.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature was then increased to 160° C. Reaction was maintained at 160° C. for 1.5 hours.

The molecular weights were determined by GPC using Dichloromethane as solvent. The results were as follows: Mn=31.5 kiloDaltons and Mw=47.6 kiloDaltons.

EXAMPLE 4

Preparation of Poly-Trimethylene Carbonate Initiated by 1,3-Propanediol

The reaction apparatus was comprised of a 1-neck 250 ml boiling flask equipped with a 90° connector and a magnetic stir bar. The apparatus was flame dried under nitrogen. An initial charge of 200.2 grams (1.96 moles) of trimethylene carbonate, 0.943 milliliters ($1.307 \times 10^{-2}$ moles) 1,3-propanediol, and 1.4 milliliters ($2.8 \times 10^{-4}$ moles) of a 0.2 M solution of stannous octoate catalyst in toluene was added to the flask.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature was then increased to 160° C. Reaction was maintained at 160° C. for 1 hour.

The molecular weights were determined by GPC using Dichloromethane as solvent. The results were as follows: Mn=32.4 kiloDaltons and Mw=57.4 kiloDaltons.

EXAMPLE 5

Preparation of 20/80 (50/50 ε-Caprolactone/Trimethylene Carbonate)/l-Lactide Segmented Copolymer The reaction apparatus was comprised of a 1 L stainless steel kettle with a 3-neck glass lid equipped with an overhead mechanical stirring unit, vacuum adapter, and two 90° connectors for an argon inlet. After obtaining a vacuum of 0.3 mmHg, the apparatus was flame dried. An initial charge of 47.5 grams (0.438 moles) 50/50 ε-caprolactone/ trimethylene carbonate from example 1 and 253 grams (1.754 moles) l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting of the contents after 30 minutes, the temperature of the oil bath was lowered to 110° C. After the 30 minutes at 110° C., 0.235 ml ($4.693 \times 10^{-5}$ moles) of a 0.2 M solution of stannous octoate catalyst in toluene was added to the kettle while stirring. The temperature was then increased to 140° C., and the stir rate was decreased to 50 RPM. Stirring was stopped after 1 hour and 10 minutes. The reaction was maintained at 140° C. for 26.5 hours.

The inherent viscosity using chloroform as a solvent was 1.4 dl/g. The melting temperature and heat of fusion, as determined by differential scanning calorimetry, were 187.6° C. and 50.1 J/g, respectively.

EXAMPLE 6

Preparation of 20/80 (50/50 ε-Caprolactone/Trimethylene Carbonate)/(92/8 l-Lactide/ε-Caprolactone) Segmented Copolymer The reaction apparatus was comprised of a 1 L stainless steel kettle with a 3-neck glass lid equipped with an overhead mechanical stirring unit, vacuum adapter, and two 90° C. for an argon inlet. After obtaining a vacuum of 0.4 mmHg, the apparatus was flame dried. An initial charge of 48.0 grams (0.444 moles) of 50/50 ε-Caprolactone/ Trimethylene Carbonate from Example 1, 13 grams (0.111 moles) of ε-Caprolactone, and 240.1 grams (1.665 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after approximately 15 minutes, the temperature was decreased to 110° C. After 30 minutes 0.238 milliliters ($4.76 \times 10^{-5}$ moles) of a 0.2 M solution of stannous octoate catalyst in toluene was added to the kettle while stirring. The temperature was then increased to 140° C. and stir rate was lowered to approximately 50 rpm. Stirring was stopped after approximately 2.5 hours. The reaction was maintained at 140° C. for 26.5 hours.

The inherent viscosity using chloroform as a solvent was 1.25 dl/g. The melting temperature and heat of fusion, as determined by differential scanning calorimetry, were 175.2° C. and 59.5 J/g, respectively.

EXAMPLE 7

Preparation of 10/90 (80/20 ε-Caprolactone/Trimethylene Carbonate)/(92/8 l-Lactide/ε-Caprolactone) Segmented Copolymer The reaction apparatus was comprised of a 1 L stainless steel kettle with a 3-neck glass lid equipped with an overhead mechanical stirring unit, vacuum adapter, and two 90° C. for an argon inlet. After obtaining a vacuum of 0.35 mmHg, the apparatus was flame dried. An initial charge of 25.1 grams (0.216 moles) of 80/20 ε-caprolactone/ trimethylene carbonate from Example 2, 18.3 grams (0.156 moles) of ε-caprolactone, and 258.6 grams (1.793 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after 5 minutes, the temperature was decreased to 110° C. After 30 minutes 0.385 milliliters ($7.71 \times 10^{-5}$ moles) of a 0.2 M solution of stannous octoate catalyst in toluene was added to the kettle while stirring. The temperature was then increased to 140° C. and stir rate was lowered to approximately 40 rpm. Stirring was stopped after approximately 2 hours. The reaction was maintained at 140° C. for 26.5 hours.

The inherent viscosity using chloroform as a solvent was 2.46 dl/g. The melting temperature and heat of fusion, as determined by differential scanning calorimetry, were 176.2° C. and 42.7 J/g, respectively.

EXAMPLE 8

Preparation of 30/70 (80/20 ε-Caprolactone/Trimethylene Carbonate)/(92/8 l-Lactide/ε-Caprolactone) Segmented Copolymer The reaction apparatus was comprised of a 1 L stainless steel kettle with a 3-neck glass lid equipped with an overhead mechanical stirring unit, vacuum adapter, and two 90° C. for an argon inlet. After obtaining a vacuum of 0.35 mmHg, the apparatus was flame dried. An initial charge of 75.6 grams (0.6787 moles) of 80/20 ε-caprolactone/ trimethylene carbonate from Example 2, 14.6 grams (0.1267 moles) of ε-caprolactone, and 210.1 grams (1.457 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after 5 minutes, the temperature was decreased to 110° C. After 30 minutes 0.081 milliliters ($1.62 \times 10^{-5}$ moles) of a 0.2 M solution of stannous octoate catalyst in toluene was added to the kettle while stirring. The temperature was then increased to 140° C. and stir rate was lowered to approximately 40 rpm. Stirring was stopped after approximately 40 minutes. The reaction was maintained at 140° C. for 26.5 hours.

The inherent viscosity using chloroform as a solvent was 1.2 dl/g. The melting temperature and heat of fusion, as determined by differential scanning calorimetry, were 169.3° C. and 43 J/g, respectively.

EXAMPLE 9

Preparation of 10/90 Poly-$\epsilon$-Caprolactone/(95/5 l-Lactide/Trimethylene Carbonate) Segmented Copolymer The reaction apparatus was comprised of a 1 L stainless steel kettle with a 3-neck glass lid equipped with an overhead mechanical stirring unit, vacuum adapter, and two 90° connectors for an argon inlet. After obtaining a vacuum of 0.5 mmHg, the apparatus was flame dried. An initial charge of 24.8 grams (0.2157 moles) of poly-$\epsilon$-caprolactone from Example 3, 10.1 grams (0.0971 moles) of trimethylene carbonate, and 265.8 grams (1.8442 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 100 rpm. Upon complete melting and mixing of the contents after 10 minutes, the temperature was decreased to 110° C. After 30 minutes 0.385 milliliters (7.705×10$^{-5}$ moles) of a 0.2 M solution of stannous octoate catalyst in toluene was added to the kettle while stirring. The temperature was then increased to 140° C. and stir rate was lowered to approximately 40 rpm. Stirring was stopped after approximately 2.5 hours. The reaction was maintained at 140° C. for 26.5 hours.

The inherent viscosity using chloroform as a solvent was 2.16 dl/g. The melting temperature and heat of fusion, as determined by differential scanning calorimetry, were 176.8° C. and 54 J/g, respectively.

EXAMPLE 10

Preparation of 10/90 Trimethylene Carbonate/(95/5 l-Lactide/Trimethylene Carbonate) Segmented Copolymer The reaction apparatus was comprised of a 1 L stainless steel kettle with a 3-neck glass lid equipped with an overhead mechanical stirring unit, vacuum adapter, and two 90° C. for an argon inlet. After obtaining a vacuum of 0.35 mmHg, the apparatus was flame dried. An initial charge of 22.2 grams (0.2175 moles) of poly-trimethylene carbonate from example 4, 10 grams (0.0979 moles) of trimethylene carbonate, and 267.9 grams (1.8596 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after 25 minutes, the temperature was decreased to 110° C. After 30 minutes 0.389 milliliters (7.768×10$^{-5}$ moles) of a 0.2 M solution of stannous octoate catalyst in toluene was added to the kettle while stirring. The temperature was then increased to 140° C. and stir rate was lowered to approximately 40 rpm. Stirring was stopped after approximately 1 hour. The reaction was maintained at 140° C. for 26.5 hours.

The inherent viscosity using chloroform as a solvent was 2.85 dl/g. The melting temperature and heat of fusion, as determined by differential scanning calorimetry, were 181.7° C. and 40.3 J/g, respectively.

EXAMPLE 11

Physical Breaking Strength Properties and Data of Representative Fibers Made From Copolymers in Examples 5 through 10.

Prior to extruding polymers were dried under vacuum at 40° C. for over 8 hours followed by 80° C. for at least 4 hours. The copolymers were extruded using a ½" single screw extruder. Zone 1 temperature ranged from 125° C. to 175° C. Zone 2 temperature ranged from 175° C. to 220° C. Zone 3 temperature ranged from 195° C. to 230° C. Die temperature ranged from 200° C. to 230° C. Temperatures were dependent on polymer copolymer viscosity. The extrudates were the n oriented by drawing 4× to 12× in 2 stages using temperatures of 45° C. to 90° C. and 53° C. to 105° C. for the first and second stages respectively. Thermal and/or tensile properties of representative undrawn and/or drawn fibers are summarized in Table I. Selected drawn monofilaments of copolymers in Examples 5 through 10 were incubated at 37° C. in a phosphate buffer solution at pH of 7.4. The percent strength retention data are included in Table I.

TABLE I

Properties of Representative Fibers

| Example | $T_C$ (° C.) | $T_m$ (° C.) | $\Delta H_f$ (J/g) | Tensile Strength (kpsi) | Modulus (kpsi) | Elongation (%) | % BSR at week 6 | % BSR at week 12 |
|---|---|---|---|---|---|---|---|---|
| 5 | 87.8 | 172.2 | 47 | 90.2 | 683 | 53 | 44 | 40 |
| 6 | 113.6 | 165.9 | 33.8 | 80 | 525 | 59 | — | — |
| 7 | 111 | 164.6 | 30.9 | 84 | 574 | 47 | 62 | — |
| 9 | 118.4 | 169.2 | 28.6 | 106.3 | 647 | 41 | — | — |
| 10 | 103.8 | 167.8 | 26.4 | 96.2 | 726.5 | 37.3 | — | — |

EXAMPLE 12

Preparation of 20/80 Poly-$\epsilon$-Caprolactone/(95/5 l-Lactide/Trimethylene Carbonate) Segmented Copolymer The reaction apparatus was comprised of a 250 ml round glass boiling flask equipped with a three-way Claisen type adapter, an overhead mechanical stirring unit, and a 90° connector for a vacuum/argon connection. An initial charge of 16.8 grams (0.14672 moles) of poly-$\epsilon$-caprolactone prepared as described in Example 3, 3.0 grams (0.02934 moles) of trimethylene carbonate, and 80.3 grams (0.55754 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 45 rpm. Stirring was stopped after approximately 5 hours. The reaction was maintained at 140° C. for 72 hours.

The inherent viscosity using chloroform as a solvent was 1.13 dl/g. The melting temperature and heat of fusion, as determined by differential scanning calorimetry, were 172.6° C. and 58.6 J/g, respectively.

EXAMPLE 13

Preparation of 92/8 L-Lactide/ Trimethylene Carbonate Polymer

The reaction apparatus was comprised of a 1 L stainless steel kettle with a 3-neck glass lid equipped with an overhead mechanical stirring unit, vacuum adapter, and a 90° connector for an argon inlet. After obtaining a vacuum of 0.5 mmHg, the apparatus was flame dried. An initial charge of 29.3 grams (0.2844 moles) of trimethylene carbonate, and 471 grams (3.2706 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 110° C. and stirring initiated at 120 rpm. Upon complete melting and mixing of the contents after approximately one hour, 0.452 milliliters ($2.37 \times 10^{-3}$ moles) of decyl alcohol and 0.889 milliliters ($1.7775 \times 10^{-4}$ moles) of a 0.2 M solution of stannous octoate catalyst in toluene were added to the kettle while stirring. The temperature was then increased to 140° C. and stir rate was lowered to approximately 40 rpm. Stirring was stopped after approximately 45 minutes. The reaction was maintained at 140° C. for 48 hours.

The inherent viscosity using chloroform as a solvent was 3.53 dl/g. The melting temperature and heat of fusion, as determined by differential scanning calorimetry, were 182.7° C. and 59 J/g, respectively.

EXAMPLE 14

Preparation of Poly-Trimethylene Carbonate Initiated By 1,3-Propanediol

The reaction apparatus was comprised of a 1-neck 250 ml boiling flask equipped with a 90° connector and a magnetic stir bar. The apparatus was flame dried under nitrogen. An initial charge of 350 grams (3.431 moles) of trimethylene carbonate, 1.738 g ($2.287 \times 10^{-2}$ moles) 1,3-propanediol, and 1.7155 milliliters ($1.7155 \times 10^{-3}$ moles) of a 0.1 M solution of stannous octoate catalyst in toluene was added to the flask.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature was then increased to 150° C. Reaction was maintained at 150° C. until the monomer conversion was complete. This was verified by GPC using Dichloromethane as a solvent.

EXAMPLE 15

Preparation of 8/92 Trimethylene Carbonate/(96/4 l-Lactide/Trimethylene Carbonate) Segmented Copolymer The reaction apparatus was comprised of a 1 L stainless steel kettle with a 3-neck glass lid equipped with an overhead mechanical stirring unit, vacuum adapter, and two 90° C. for an argon inlet. After obtaining a vacuum of 0.35 mm Hg, the apparatus was flame dried. An initial charge of 58.7 grams (0.575 moles) of poly-trimethylene carbonate from Example 14, 27.0 grams (0.265 moles) of trimethylene carbonate, and 914.3 grams (6.349 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after 25 minutes, the temperature was decreased to 110° C. After 30 minutes, the temperature was then increased to 140° C. and stir rate was lowered to approximately 40 rpm. Stirring was stopped after approximately 1 hour. The reaction was maintained at 140° C. for 60 hours. At the conclusion of the reaction, the polymer was isolated, ground, and characterized as described for the copolymer of Example 10.

EXAMPLE 16

Preparation of 8/92 Trimethylene Carbonate/(98/2 l-Lactide/Trimethylene Carbonate) Segmented Copolymer The reaction apparatus was comprised of a 1 L stainless steel kettle with a 3-neck glass lid equipped with an overhead mechanical stirring unit, vacuum adapter, and two 90° C. for an argon inlet. After obtaining a vacuum of 0.35 mm Hg, the apparatus was flame dried. An initial charge of 58.7 grams (0.575 moles) of poly-trimethylene carbonate from Example 14, 13.5 grams (0.1325 moles) of trimethylene carbonate, and 933.3 grams (6.4813 moles) of l-lactide was added to the kettle.

The copolymerization polymer isolation, and characterization was conducted as in Example 15.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all sub-ranges of all ranges disclosed herein. These sub-ranges are also useful in carrying out the present invention.

What is claimed is:

1. A crystalline copolymer comprising
   a copolymer of l-lactide and at least one cyclic monomer, said cyclic monomer comprising a liquid at or above about 40° C.,
   wherein the l-lactide derived sequences of the polymer chain are crystallizable segments or blocks and comprise from about 60 to about 99 percent of all sequences, and wherein the copolymer has a $T_m$ of at least 150° C., exhibits a crystallinity of at least about 20%, and has an inherent viscosity of at least about 1.1 dl/g.

2. The copolymer set forth in claim 1 wherein the cyclic monomer comprises ϵ-caprolactone.

3. The copolymer set forth in claim 2 wherein the ϵ-caprolactone derived sequences of the polymer chain comprise from about 25 to about 9 percent of all sequences.

4. The copolymer set forth in claim 3 wherein the ϵ-caprolactone derived sequences of the polymer chain comprise about 20 percent of all sequences.

5. A monofilament suture made from the copolymer of claim 2 having an elastic modulus of greater than about 100,000 psi, a tensile strength of greater than about 40,000 psi, and a percent elongation of less than about 80%.

6. A multifilament yarn comprising the copolymer of claim 2.

7. A surgical suture comprising the multifilament yarn of claim 6.

8. A surgical device or construct comprising the multifilament yarn of claim 6 in the form of a mesh, a prosthetic tendon, a ligament or a vascular graft.

9. The copolymer set forth in claim 1 wherein the cyclic monomer comprises trimethylene carbonate.

10. The copolymer set forth in claim 9 further comprising ϵ-caprolactone derived polymer sequences.

11. A monofilament suture made from the copolymer of claim 9 having an elastic modulus of greater than about 100,000 psi, a tensile strength of greater than about 40,000 psi, and a percent elongation of less than about 80%.

12. A multifilament yarn comprising the copolymer of claim 9.

13. A surgical suture comprising the multifilament yarn of claim 12.

14. A surgical device or construct comprising the multifilament yarn of claim 12 in the form of a mesh, a prosthetic tendon, a ligament or a vascular graft.

* * * * *